United States Patent [19]

Crawford

[11] Patent Number: 4,713,340
[45] Date of Patent: Dec. 15, 1987

[54] BIODEGRADATION OF PENTACHLOROPHENOL

[75] Inventor: Ronald L. Crawford, Mound, Minn.

[73] Assignee: Regents of the University of Minnesota, St. Paul, Minn.

[21] Appl. No.: 620,231

[22] Filed: Jun. 13, 1984

[51] Int. Cl.$^4$ .......................... C12N 1/20; C12R 1/20
[52] U.S. Cl. .................................. 435/253; 435/850;
435/262; 435/277; 210/611; 210/909
[58] Field of Search ............... 435/253, 850, 248, 813,
435/262, 264, 277; 424/353; 514/751, 758;
210/611, 909

[56] References Cited

U.S. PATENT DOCUMENTS 3,310,477 3/1967 Wilke .................................. 435/813

OTHER PUBLICATIONS

D. L. Saber and Ronald L. Crawford, *Applied and Environmental Microbiology*, 50, 1512, (Dec., 1985).
R. U. Edgehill et al., Applied and Environmental Microbiology, 45, 1122, (1983).
R. U. Edgehill et al., European J. Applied Microbiol. Biotechnol., 16, 179, (1982).
I. Watanabe, Soil Sci. Plant Nutr., 19, 109, (1973).
T. Suzuki, J. Environ. Sci. Health, B12, 113 (1977).
J. J. Pignatello et al., Applied and Environ. Microbiol., 46, 1024, (Nov. 1983).
B. Rott et al., J. Agric. Food Chem., vol. 27, No. 2, (1979), pp. 306–310.
*Bergeys Manuel of Determinative Bacteriology*, Eighth Edition, 1974, pp. 357–359.
*Pesticide Disposal and Detoxification*, Editor A. P. Dillon, Noyes Data Corporation, 1981, pp. 66–69 and 252–255.

Primary Examiner—John E. Tarcza
Attorney, Agent, or Firm—Merchant, Gould, Smith, Edell, Welter & Schmidt

[57] ABSTRACT

A bacterium of the genus Flavobacterium which utilizes pentachlorophenol (PCP) as its sole carbon and energy source, which tolerates media PCP concentrations over about 250 mg/l, and which may be used in methods of detoxifying PCP-contaminated material.

10 Claims, 6 Drawing Figures

BIODEGRADATION OF PENTACHLOROPHENOL

U.S.E.P.A. SUPPORT

This invention was made with Government support under Contract Number CR-810-01-60-10, awarded by the U.S. Environmental Protection Agency. The Government has certain rights in the invention.

BACKGROUND OF THE INVENTION

This invention relates to methods of biologically degrading pentachlorophenol.

Pentachlorophenol (PCP) is a widely used biocide which has been reported to uncouple oxidative phosphorylation, to complex with respiratory proteins in mitochondria, and to inhibit active transport of ions in bacteria [Edgehill et al., Eur. J. Appl. Microbiol. *Biotechol.*, 16, 179-184 (1982)]. It has been applied to crops as a herbi-cide, and it is also used as an insecticide, fungicide, an algicide and a disinfectant. PCP is particularly widely used as a wood preservative, to inhibit molds and wood boring insects.

Due to its widespread use and its acute toxicity (many species of fish are reportedly killed at PCP concentrations of 0.6 mg/l or less), it is important to prevent build-up as a result of any of the above uses; the soil and water adjacent wood treatment plants or adjacent structures that include treated wood are particularly vulnerable to PCP contamination.

Certain bacteria have been reported to degrade PCP. However, PCP toxicity reportedly is not limited to any particular species, and PCP-degrading bacteria exhibit a limited tolerance for PCP.

Edgehill et al., report isolation of an *Arthrobacter* which exhibits constant growth in concentrations of PCP between 10-135 mg/l [Edgehill et al., supra; Edgehill et al., *Applied and Environmental Microbiol,* 45, 1122-1125 (1983)].

Watanabe, *Soil Sci. Plant Nutr.,* 19, 109-116 (1973), reports a bacteria of genus considered to be Pseudomonas or a closely related genus, which degrades PCP, grows optimally at concentrations below 100 ppm, and exhibits no growth at PCP concentrations of 200 ppm.

Suzuki, *J. Environ. Sci. Health,* B12(2), 113-127 (1977), discloses isolation of a Pseudomonad which degrades PCP at PCP concentrations of 40 mg/l but exhibits a lagged growth period when the PCP concentration exceeds that level.

SUMMARY OF THE INVENTION

I have discovered that certain bacteria of the genus Flavobacterium are tolerant of high PCP concentrations. For example, these bacteria exhibit substantially constant growth at PCP solution concentrations of 250 mg/l and above, and can utilize PCP as their sole source of carbon and energy. The invention discloses the isolation and characterization of these bacteria and their use in a method to detoxify PCP-contaminated materials by microbial degradation.

In preferred embodiments, the bacterium is isolated and then grown aerobically in a medium containing a non-PCP carbon/energy source such as glutamic acid, or some other conventional growth substrate, and the PCP pathway is induced by adding relatively small amounts of PCP to the medium.

Preferred embodiments of the bacterium comprise a yellow insoluble pigment, grow optimally at temperatures of about 20°-37° C., preferably between about 25°-30° C., and will maintain growth in the presence of PCP concentrations up to about 400 mg/l.

The bactera of the present invention permit highly effective detoxification of many types of PCP contamination, particularly those in which the dissolved PCP concentration exceeds about 250 mg/l. It is expected that methods known to the art could be employed to produce mutations of the biologically pure strain described herein which would also posses useful properties with respect to the degradation of PCP or other chlorinated biocides.

Solid material such as soil and wood chips may be decontaminated by an extractive process which preferably is operated so as to bring the bacteria of this invention into contact with aqueous solutions having PCP concentrations of, e.g., about 100-250 mg/l. These aqueous solutions are obtained by continuously or intermittently leaching the solid material with pH-controlled water comprising the PCP-degrading bacterium. Surface and ground water may also be detoxified, by inoculating the water with an effective amount of the present bacterium.

Other features and advantages of the invention will be apparent from the following detailed description and appended claims.

DETAILED DESCRIPTION OF THE INVENTION

The Bacterium

Figure 1:
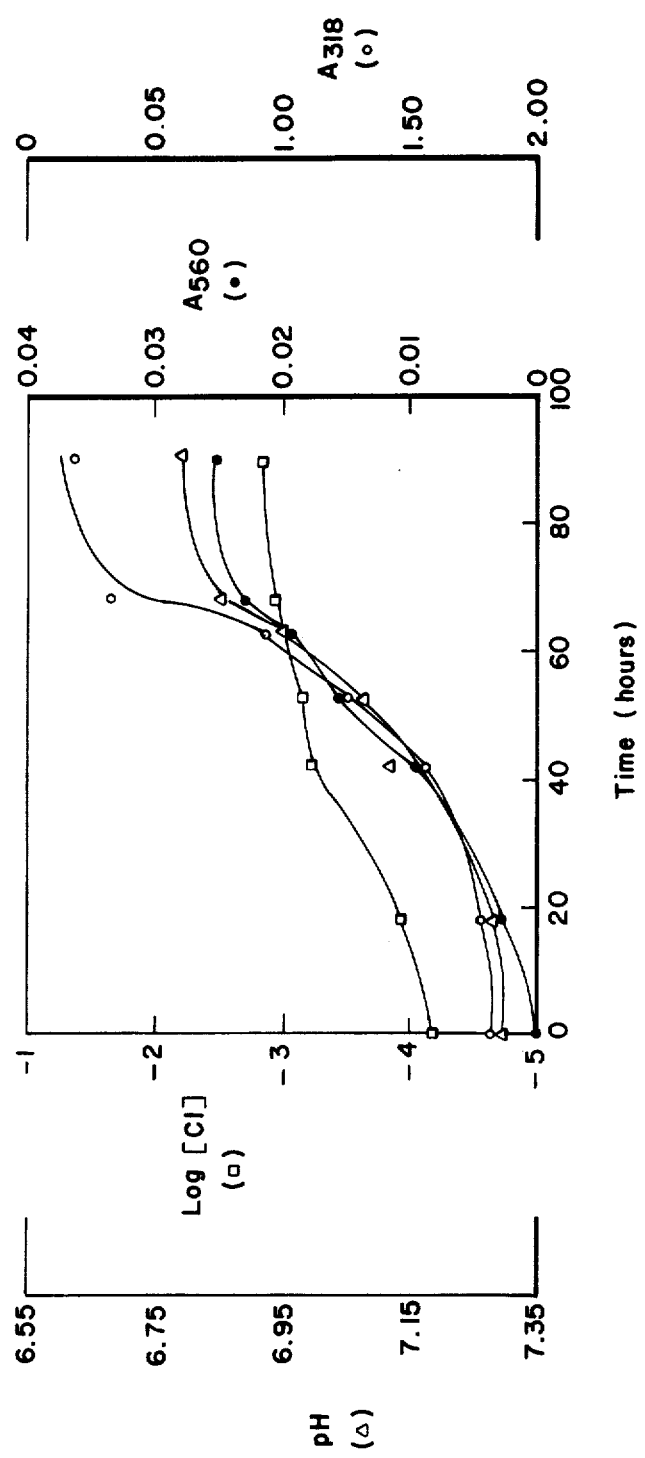
FIG. 1 is a graphic representation summarizing parameters associated with the growth of a pure bacterial culture of the present invention employing PCP as the sole carbon and energy source.

The PCP-degrading bacterium of the present invention is a member of the genus Flavobacterium having the characteristics as set forth in Table I, below.

TABLE I

| Characteristics of PCP-Degrading Flavobacterium | |
|---|---|
| Morphology: | Rod-shaped, approximately 2 micrometers in length, nondiffusable pigmentation, not motile. Light to heavy pellicle developed upon stationary growth. Possesses cytoplasmic incursions when grown on rich media. |
| Gram Stain: | Negative |
| Physiology: | Positive with respect to: |
| | Oxidase, catalase, phosphatase |
| | Negative with respect to: |
| | Casein hydrolysis |
| | Gelatin hydrolysis |

TABLE I-continued
Characteristics of PCP-Degrading Flavobacterium

| | |
|---|---|
| | Lipase |
| | Amylase |
| | Arginine dihydrolase |
| | Nitrogen production from nitrate. |
| | Indole production |
| | Urea hydrolysis |
| | Citrate utilization |
| | MRVP test |
| | Modification of litmus milk medium. |
| | DNase production |
| | No growth on N-free base. |
| | No growth on MacConkey Agar. |
| | Cellulase production. |
| | Agar degradation |
| | Growth at 40° C. |
| Tolerance: | Can grow in up to 2% NaCl. |
| Growth Characteristics: | Tends to be microaerophilic and will ferment the following in the presence of low-oxygen (acid production in OF-test): |
| | glucose     maltose |
| | trehalose    salicin |
| | cellobiose |
| | Under strict anaerobic conditions, it will not ferment glucose. |
| | Produces ammonia when grown on peptone. |
| | No acide production (OF-test) aerobically with following C-sources: |
| | xylose      galactose |
| | mannose    salicin |
| | fructose    inulin |
| | maltose     glycerol |
| | sorbose     sorbitol |
| Carbon Sources Utilized: | Is nutritionally limited; carbon sources include: |
| | glucose      inulin |
| | gluconate*   galactose |
| | mannose     salicin |
| | butyrate     dextrin |
| | maltose      cellobiose |
| | acetate      pyruvate |
| | succinate    aspartate |
| | beta-hydroxy-butyrate |
| Carbon Sources Not Utilized:** | Will not utilize: |
| | sucrose       propionate |
| | lactose        salicylate |
| | rhamnose    valerate |
| | manitol       oxalate |
| | raffinose     ethanol |
| | arabinose    propanol |
| | ducitol       citrate |
| | inositol       trehalose |
| | glucosamine  benzoate |
| | malonate     glycine |
| | tartarate     fumarate |
| | B-alanine    starch |
| | fructose     arginine |
| | 2-chlorobenzoate |
| | 3-chlorobenzoate |
| | 2,4-dichlorobenzoate |
| | 4,6-dichlororesorcinol |
| | o-chlorophenol |
| | m-chlorophenol |
| | p-chlorophenol |
| | 2,4-dichlorophenol |
| | 2,4-dichlorophenoxyacetic acid |
| Resistance: | Resistant to novobiocin at disc. concentration of 30 mcg (standard BBL disc). |
| DNA: | The cytosine and guanine content of the bacterium's |

TABLE I-continued
Characteristics of PCP-Degrading Flavobacterium

| |
|---|
| purified DNA is 63%. |

*Organic acids tested as sodium or equivalent nontoxic salt.
**Compounds supplied as only carbon source at concentrations of 100 mg/l in medium of Ex. I.

The bacterium is further characterized in that it tolerates and grows in media having relatively high solution concentrations of PCP. As used herein, "tolerating" means that the growth rate is not substantially reduced by such concentrations. Specifically, the organism grows at a steady rate at PCP levels between about 300 and 350 mg/l, and, even for PCP concentrations up to about 400 mg/l, the organism survives. As used herein, the term "solution" as used with respect to PCP refers to dissolved PCP in the salt- or anionic form.

The organism rapidly degrades PCP to non-toxic material, such as chloride ions and carbon dioxide. For example, solution PCP levels of 300 mg/l are degradable in 8–10 hours.

The optimum growth of the bacterium takes place within a pH range of about 6.9–8.5, preferably from about 7.0 to 7.4, and within a temperature range of about 15°–40° C., preferably about 20°–37° C., most preferably about 25°–30° C. The organism does not comprise measurable amounts of a fluorescent component.

EXAMPLE I

Isolation of Bacterium

The preferred strain for use in the present method was isolated from freshwater sediments of collection pools in artificial channels constructed along the Mississippi River at Monticello, Minn. Each channel is 520 m long with 0.14 hectare of water surface area, and has nine sediment pools, consisting of fine sandy loam to course sand, each of which is 3.4–3.5 m wide and about 0.58 m deep.

A PCP-supplemented growth medium was percolated through a column filed with pool sediment at pH 7.0–7.4. A satisfactory medium is as follows:

5.88 mM $NaNO_3$,
3.6 mM $K_2HPO_4$,
1.4 mM $KH_2PO_4$,
0.4 mM $MgSO_4.7H_2O$,
40 mg/l PCP (93.7% PCP, Dow Chem. Co.).

The molar concentration of nutrients in the medium may be increased or decreased by factors of about 3–5, if necessary, in order to enhance the detection of the desired bacteria. Disappearance of PCP was monitored by observing a decrease in absorbance of the column effluent at 318–320 nm vs. distilled water in 1 cm cells (Bausch and Lomb Spectronic 710 spectrophotometer). Once a decline in absorbance was observed, a portion of the effluent was used to inoculate a liquid shake-flask culture of the same medium. Degradation of PCP in the shake-flask was followed by monitoring absorbance of the medium at 320 nm and by observing release of chloride ions using a chloride-specific ion electrode. The electrode was used by the method provided in *Orion: Analyzer Instruction Manual* (Model 94-17); Low-level measurements using 701A digital pH/mv meter-chloride, the disclosure of which is incorporated by reference herein. Once degradation was noted, an inoculating loop was used to streak from the liquid culture onto plated media (same growth medium +1.5% purified agar). The plates were incubated at 25°–30° C. until isolated colonies appeared. Isolated colonies were then transferred to "indicator agar" plates (same medium but with the addition of a pH indicator, Bromothymol Blue). Colonies that dechlorinate PCP produced a color change due to HCl formation. These colonies were restreaked until pure. Pure cultures grew rapidly on PCP-containing media, releasing all of PCP's chlorine as chloride ions. This purified culture has been deposited with the American Type Culture Collection and has been assigned ATCC No. 39723 (Strain L-1).

FIG. 1 summarizes parameters associated with the growth of a pure bacterial culture of the present invention on PCP as the sole source of carbon and energy. The bacterium was grown at 30° C. in the mineral salts medium described hereinabove, which contained PCP at 100 mg/l. PCP removal was complete in about 90 hours with all the organic chlorine being released as chloride ion. Symbols: Δ, pH; □, log chloride ion concentration (molar); O, absorbance at 560 nm (culture turbidity); O, absorbance at 318 nm (PCP concentration). In the examples given below, this biologically pure strain was employed.

EXAMPLE II

Cultivating the Strain

Once the pure strain was isolated, it was cultivated to increase the number of cells and to induce the PCP-degradation pathway by axenically growing the cells in the above-described basal medium containing 4.0 g/l glutamic acid as the growth substrate instead of PCP (a range of about 15 g glutamic acid/l was found to be satisfactory; about 4.0 g/l is preferred). Other conventional growth substrates also may be used. Cell densities in the initial inocula were determined by direct microscopic counts by the method of Hobbie et al., *Appl. Environ. Microbiol.*, 33, 1225 (1977), the disclosure of which is incorporated herein by reference. When the cells reached a density of $1 \times 10^9$ cells per ml, PCP was added at a concentration of 20 mg per ml to induce the PCP-degrading mechanism in the cells (20–40 mg of PCP per ml of medium is an effective inducer). The disappearance of PCP was measured by following the UV absorbance at 318–320 nm according to the procedure of Pignatello et al., *Appl. Environ. Microbiol.*, 46, 1024 (1983), the disclosure of which is incorporated by reference herein.

Once the cells started to actively degrade PCP, the cell-containing nutrient broths were used to directly inoculate the treatment tanks described below to afford a final concentration of $1 \times 10^6$ to $1 \times 10^7$ cells/ml in the treatment medium or leachate.

Detoxification

A. Water

The ability of the above-described bac-teria to degrade PCP provides a safe and effective means for detoxification of PCP-contaminated media and materials.

Bacteria which have been induced to degrade PCP are added to contaminated aqueous solutions maintained within the appropriate pH range, preferably over 6.9 and most pre-ferably about 7.0–8.0, to afford optimal degradation con-ditions for the bacteria while maintaining the PCP in its ionized, more soluble salt form. Concentrations of PCP in water samples were determined by the gas chromatography pro-cedure disclosed by Pignatello et al., in *Appl. Environ. Microbiol.*, 46, 1024 (1983), the disclosure of which is incorporated by reference herein. The water temperature range is maintained at levels that maximize PCP degradation, preferably about 20–37° C., and most preferably about 25°–30° C.

Water, either from ground or surface sources, is typically detoxified by pumping it into treatment tanks or ponds, where the bacterial broth is added to afford a concentration of about $1 \times 10^6$–$1 \times 10^8$ cells/ml of water. A pump can be used to bubble air or oxygen through the treatment container for proper aeration. The pH and temperature are monitored regularly and maintained within the ranges set forth hereinabove. This method is effective to substantially degrade PCP concentrations of up to about 400 mg/l of PCP within about two weeks.

EXAMPLE III

Detoxification of Natural Waters

Mississippi River water was collected (temperature of water, 20° C.; oxygen, 8 mg/l; pH, 8.2) from outdoor experimental streams at the Monticello Ecological Research Station, a field station of the U.S. Environmental Protection Agency Environmental Research Laboratory at Duluth, MN. Water (20 liters per aquarium) was distributed into all-glass, 5-gallon aquaria in 4 treatment groups. Group A (2 replicates) received water plus $10^6$ PCP-degrading bacterial cells ml$^{-1}$ of water. Group C (4 replicates) received water plus 1070–1140 micrograms/l of PCP (average = 1110 micrograms/l). Group D (4 replicates) received water, $10^6$ bacteria ml$^{-1}$, and PCP (1020–1110 micrograms/l, average = 1080 micrograms/l). Concentrations of PCP within the aquaria were monitored by periodic sampling of the water and determination of PCP gas-chromatographically. All aquaria were protected from exposure to direct light. After 48 hours, 10 fathead minnows (*Pimephales promelas*) were added to each aquarium, and fish survival monitored over time to 168 hours.

Numerous other water samples were collected from the vicinity of the Gray Freshwater Biological Institute, Navarre, MN. Groundwater was collected from a well in Deephaven, MN (water pH, 6.9). Oligotrophic surface water (pH 7.2) was collected from Christmas Lake. Eutrophic sur-face water (pH 6.9) was collected from Lake Minnetonka, and another river water sample was collected from the Crow River (pH 7.1) near Delano, MN. Portions (100 ml) of each sample were placed in separate 250 ml flasks, and PCP added to a final concentration of 100 mg/l. Each flask then received $10^7$ Flavobacterium cells/ml. Control flasks received only PCP. All flasks were incubated with shaking, in the dark, at 25° C. Pentachlorophenol concentrations in the various waters were determined periodically by measuring the absor-bance of small aliquots of water at 318 nm, following high-speed centrifugation to remove microbial cells. Periodic checks of PCP concentrations in noncentrifuged aliquots using gas-chromatography confirmed that decreases in $A_{318}$ were due to disappearance of PCP, not to the absorption of PCP by microbial cells.

For examination of temperature effects on rates of PCP removal, water collected from Lake Minnetonka, MN was used. Freshly-collected water (pH 6.9–7.0) was distributed into flasks (100 ml per flask) and supplemented with PCP. For temperature experiments, all flasks received 100 mg/l of PCP plus $10^7$ of the Flavobacterium cells ml$^{-1}$ and were incubated in the dark, without agitation at temperatures between 15° C. and 40° C.

Mississippi River water was distributed into aquaria as described hereinabove. All aquaria, except for treatment group A, received approximately 1 mg/l of PCP (Aldrich Chem. Co., 99% purity). Some aquaria also received bacteria, while others did not. Addition of approximately $10^6$ Flavobacterium cells ml$^{-1}$ to PCP-contaminated river water resulted in removal of greater than 90% of the biocide within 45 hours, as summarized in Table II.

TA8LE II

Removal of PCP from River Water

| Time (Treatment Group D) | % of Original PCP Remaining | |
|---|---|---|
| | Aquaria with Bacteria | Uninoculated Aquaria (in hours) (Treatment Group C) |
| 0 | 100.0 ± 4.0 | 100.0 ± 2.5 |
| 4 | 93.8 ± 4.0 | 103.2 ± 1.2 |
| 8 | 87.0 ± 2.9 | 102.8 ± 0.5 |
| 12 | 79.2 ± 7.9 | 98.3 ± 0.9 |
| 20 | 64.2 ± 9.7 | 100.5 ± 7.0 |
| 34 | 40.3 ± 14.9 | 102.0 ± 9.2 |
| 45 | 24.5 ± 15.6 | 105.5 ± 15.3 |
| 48 (fish added) | ND | ND |
| 51 | 17.4 ± 12.6 | 92.1 ± 0.5 |
| 57 | 11.7 ± 9.9 | 94.4 ± 4.8 |
| 69 | 9.3 ± 8.9 | 89.7 ± 3.8 |

ND = Not determined. Results are ± standard deviation.

Removal of the PCP detoxified the water, as shown by survival of PCP-sensitive minnows in treated water, but not in untreated water. These results are summarized in Table III, below.

TABLE III

Fish Survival in Contaminated and Decontaminated River Water

| Treatment | % Fish Survival Group (Hours, following fish addition) | | | | | | | | | | |
|---|---|---|---|---|---|---|---|---|---|---|---|
| | 0 | 2.0 | 2.5 | 3.0 | 3.5 | 4.0 | 6.0 | 9.0 | 10 | 48 | 168 |
| A (No PCP, no bacteria) | 100 | 100 | 100 | 100 | 100 | 100 | 100 | 100 | 100 | 100 | 100 |
| B (No PCP, bacteria) | 100 | 100 | 100 | 100 | 100 | 100 | 100 | 100 | 100 | 100 | 100 |
| C (PCP, no bacteria) | 0 | 100 | 90 | 47.5 | 12.5 | 7.5 | 0 | 0 | 0 | 0 | 0 |
| D (PCP, plus bacteria) | 77.5 | 77.5 | 100 | 100 | 100 | 100 | 100 | 95 | 90 | 85 | 80 |

The difference between Treatment Groups C and D after 168 hours is significant at the 95% level. Of the fish that did not survive in Treatment Group D, all were in a single, atypical aquarium; no fish were lost in 3 of 4 replicate aquaria.

The ability of the Flavobacterium of this invention to remove PCP from natural waters other than Mississippi River water was examined. The Flavobacterium readily decontaminated the four additional waters, including oligotrophic (low productivity) lake water, and another river water. The Flavobacterium completely removed about 100 mg/l of PCP from each of these natural water samples within a 40–75 hour period.

The Flavobacterium strain removed PCP from lake water optimally at temperatures between 20° C. and 30° C. Removal rates slowed somewhat at 15° C., but were still significant. No significant removal of PCP was observed at 35° C.

B. Solids

The PCP tolerance of the present bacterium can be used to particular advantage in the treatment of PCP-contaminated solid material by a process comprising contacting the PCP present in or on the solid material with water so as to extract the PCP, which is then degraded with an effective amount of the present bacterium. Preferably the solid material will be slurried or leached with water (the leachate) in order to remove the PCP therefrom. To increase the amounts of solid that can be detoxified with a given volume of leachate, the leachate preferably is intermittently or continuously recycled through the solid, thus greatly increasing the PCP levels in the collected leachate to be detoxified, and maximizing the detoxification efficiency of the bacteria.

Specifically, PCP contaminated solids such as soil, landfill or wood shavings can be detoxified by collecting the solids in a holding area, such as a pit, and leaching the PCP from the contaminated material by passing pH-adjusted water through the solids and separating the leachate from the solids, preferably via a porous solid layer positioned under the material. In the case of intermittent leaching, the water will then be passed into a collection area such as a tank, pool or the like, where it is held until reintroduced into the pit area.

As shown in FIG. 1, the holding area may comprise a pit 10 which advantageously may be formed having an inclined bottom, so as to promote the flow of the leachate through the contaminated solid. The bottom and sides of the pit are sealed or lined with a moisture impermeable substance such as a polymeric plastic film 11 to prevent seepage of leachage 27 into the surrounding earth 28. One or more areas of water-permeable, porous material 13, e.g. tile strips, are set to run the length of the pit bottom and com-municate with an area of the same or a similar porous material 20 at the lower end of the pit bottom. This area, which preferably extends across the width of the pit bottom, is connected to a discharge pipe 14. Pipe 14 carries the leachate to a treatment tank or pool 26. A layer 15 of uncontaminated sand or gravel is spread over the tile to separate the tile from the contaminated solid material 16, in order to prevent plugging. A pump 17, connected by pipe 18 to the treatment tank or pool, intermittently or continuously returns the leachate 27 into the pit through a spray head, sprinkler pipe or similar liquid distribution system 19.

The soil or other contaminated solid 16 is layered into the pit so as to evenly cover the sand layer. Lime ($CaCO_3$), not shown, may be spread on top of the soil to adjust and maintain the pH of the soil and leachate.

The treatment tank 26 should be large enough to contain an amount of leachate equal to the volume of contaminated soil. If necessary, an air pump (not shown) may be employed to bubble air through the treatment tank for proper aeration. The bacteria are added to this water, either before, or preferably after leaching has commenced, to afford the desired concentration, preferably about $1 \times 10^6 - 5 \times 10^7$ cells/ml of water. The pH of the leachate is constantly monitored to optimize its leaching efficiency, and preferably is maintained at a near neutral pH, i.e. about pH 7.0–8.0. Preferably, a substantially constant volume of leachate is continuously sprayed on top of the contaminated solid material, allowed to percolate through the solid bed, and recycled to the sprinkler head. Such a constantly-circulating system need not include a holding tank or pool, but such a unit may be included to provide a convenient means for adjusting the leachate volume, cell density, pH, etc. These treatment facilities may be sized to correspond to the total volume of solid material to be decontaminated, e.g. from about 30 m$^3$ to 250,000 m$^3$ of solid material may be contained in a single pit.

EXAMPLE IV

Soil Decontamination Field Trial

Figure 2:
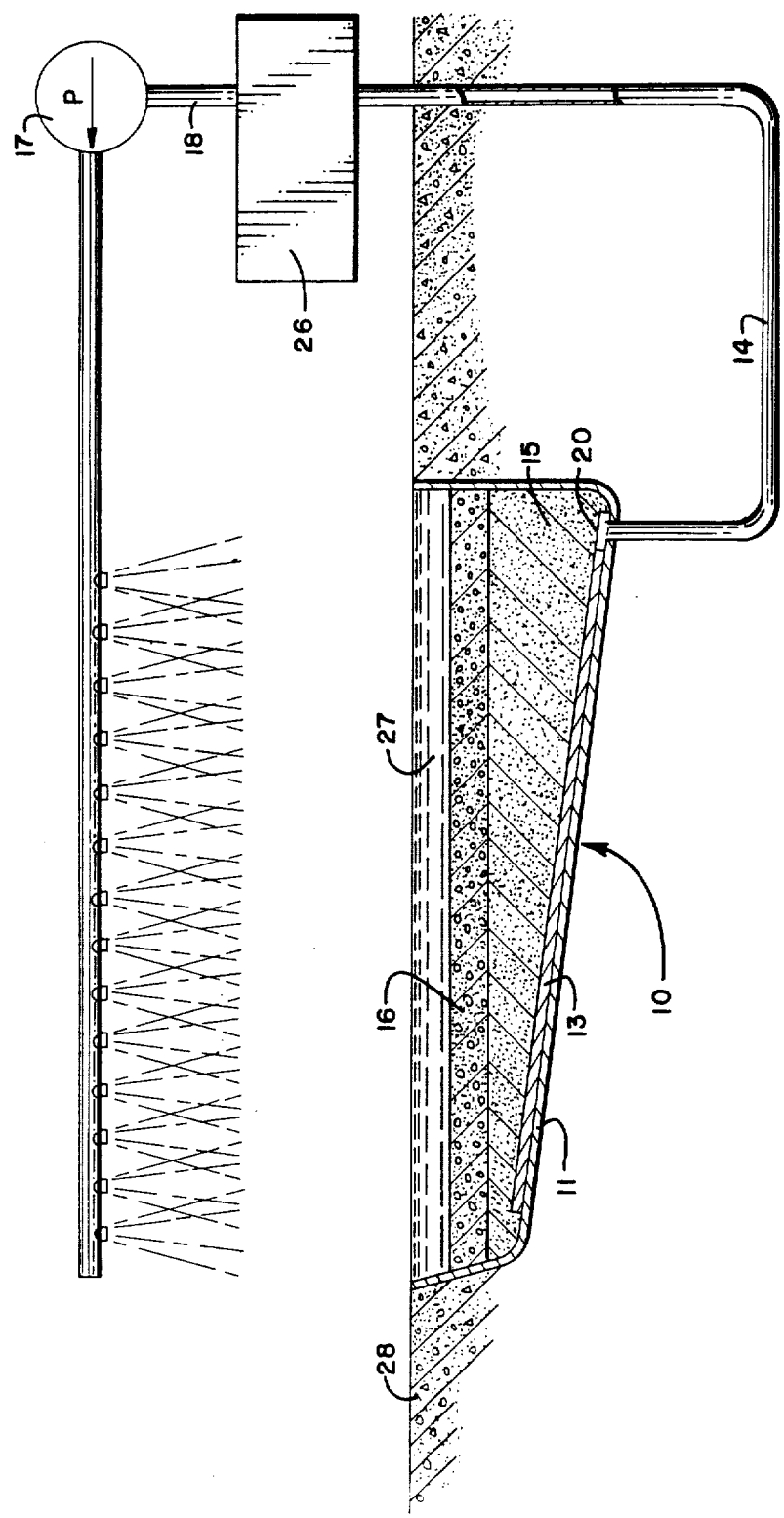
FIG. 2 is a schematic side sectional view of a recirculating system used to detoxify solid material with an aqueous leachate comprising the bacteria of the present invention.

A treatment system was designed using leaching pits similar to that shown in FIG. 2 which were treated with the PCP-degrading bacterium of the present invention. Approximately 50 m$^3$ of PCP-contaminated soil was spread over the surface of a 19.6 m square, plastic-lined pit. The pit was flooded with water containing a small amount of lime. The water percolated through the contaminated material, dissolving PCP, and was collected by gravel-covered drainage tiles placed in the bottom of the pit. Collected leachate was concentrated in a sump hole, and pumped from there into a 10,000 gal. aboveground pool. The leachate within the pool was inoculated with 100 l. of a broth containing the laboratory-grown Flavobacterium cells of the present invention yielding about 10$^6$ cells per milliliter of leachate. The pool was continuously aerated. Periodically the liquid within the pool was pumped back to the leaching pit, producing a continuously recirculating system. Two such systems were constructed, one being run as the treatment system and the other as an uninoculated control. Samples were collected from all points within the system, and examined to measure their PCP levels every week to 10 days throughout the experiment. During the course of the study several alterations were made to the original setup: (1) On day 8 a second 100 l. inoculation of the treatment pool was made; (2) Between days 24-27 the pumps of both treatment and control systems were stopped. Soil was packed around the pumps in the leaching ponds so that water could not short circuit around the soil bed. At the same time the float switches were rearranged so that, rather than maintaining a constant water level, the water level in the leaching ponds was raised and lowered as much as possible. These changes greatly increased the efficiency of leaching PCP from the soil; (3) On days 69-72 the soil in the treated leaching pond was mechanically cultivated in an attempt to release oil trapped in the soil. This resulted in an increase in the level of dissolved PCP, but was too near the end of sampling to assess its effect on the soil.

Figure 3:
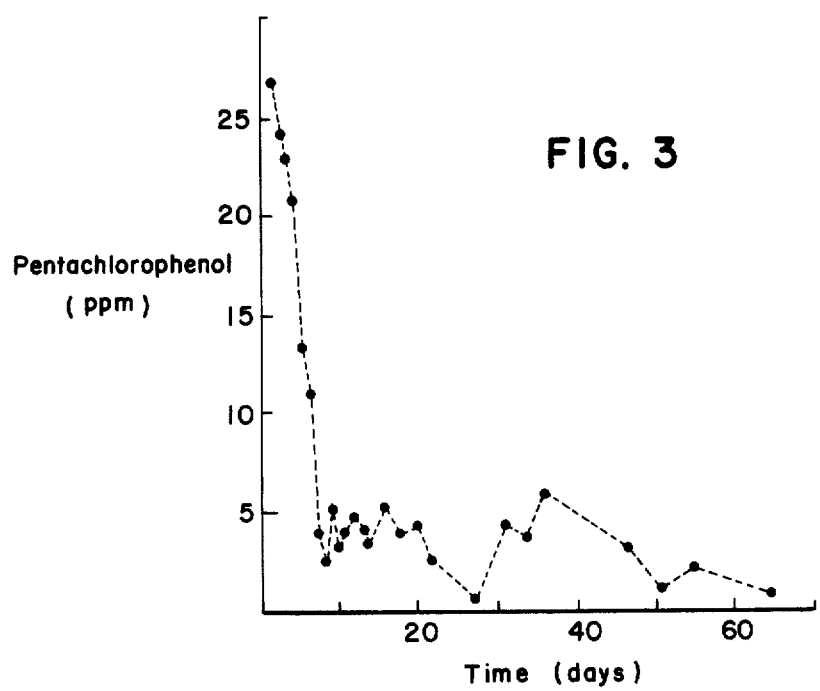
FIGS. 3 and 4 are graphic representations summarizing PCP levels in aqueous leachates comprising the bacterium of the present invention and a bacterium-free leachate, respectively, which were used to detoxify PCP-contaminated soils.
Figure 4:
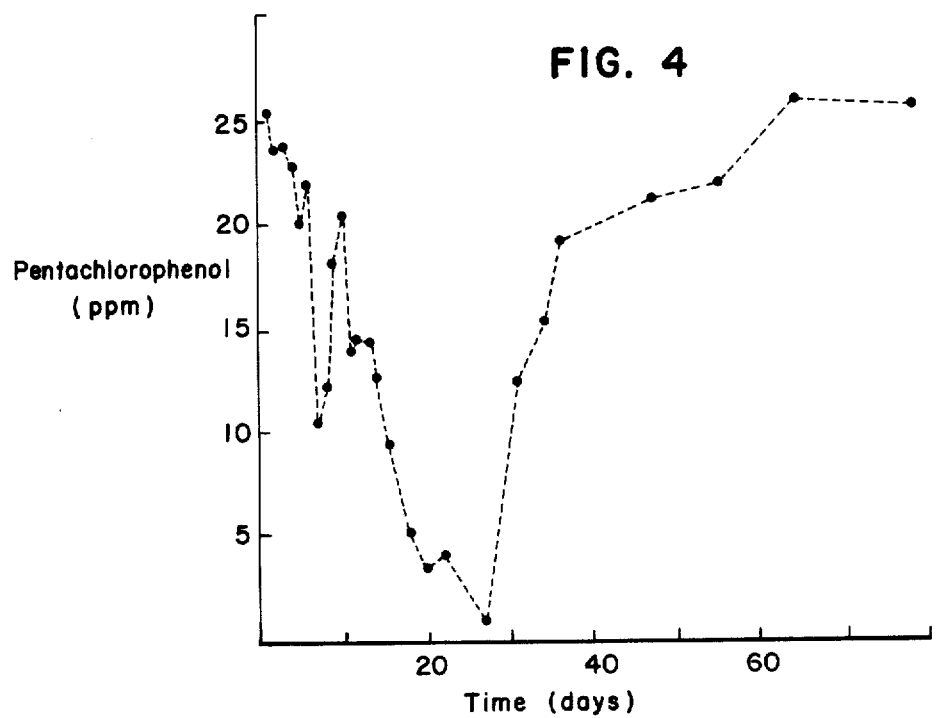

The level of dissolved PCP during the experiment is shown in FIG. 3 for the treatment pool and in FIG. 4 for the control pool. After innoculation, the level of PCP in the treatment pool dropped rapidly from 27 ppm to between 2 and 5 ppm where it remained throughout the experiment. During the initial days of the experiment the PCP level in the control pool also dropped, but the decrease was much slower than the treatment pool. (The sharp decline and recovery from day 7 to 9 is probably artifact due to heavy rains on days 7 and 8). After day 10 of the experiment, the PCP level in the control pool decreased more rapidly to between 2 and 5 ppm. When the new pumping regimen was started on day 28, the PCP level in the control pool rose steadily until it stabilized around 25 ppm. The PCP level in the inoculated pool also rose after day 28. However, it never exceeded 5 ppm.

Figure 5:
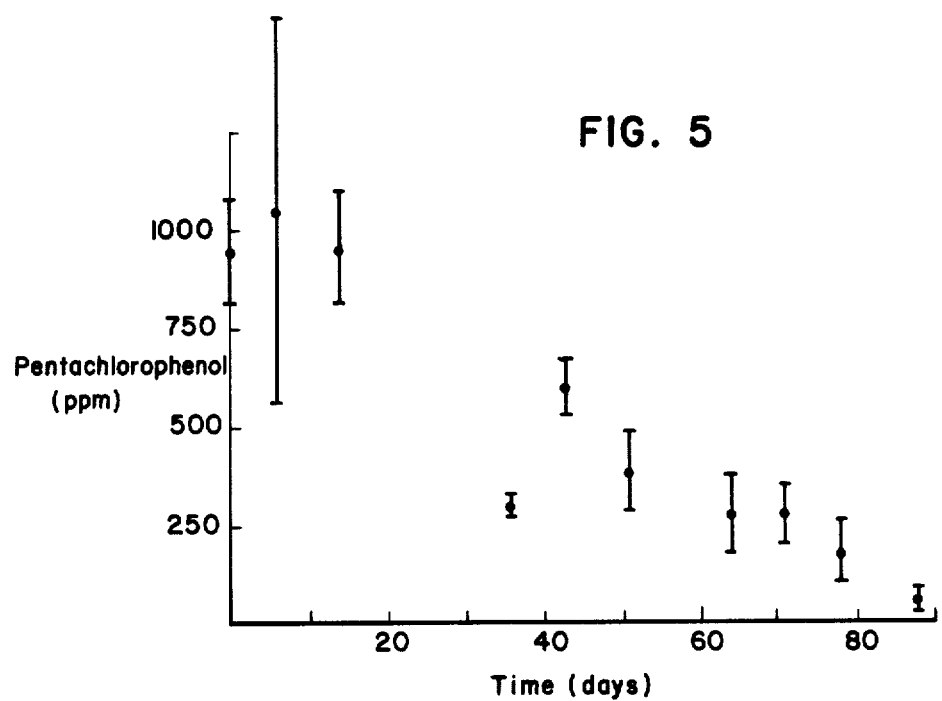
FIGS. 5 and 6 are graphic representations summarizing PCP levels in contaminated soils treated with the leachates of FIGS. 3 and 4.
Figure 6:
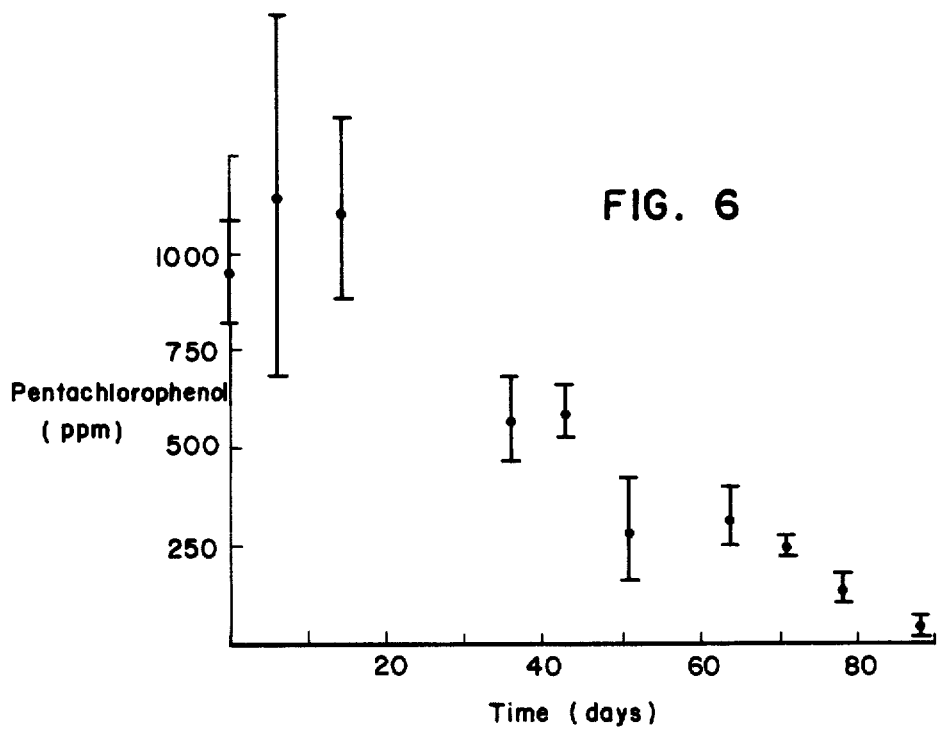

The results of PCP analyses of soil during the course of the experiment are shown in FIGS. 5 and 6 for the treatment pit and control pit, respectively. As can be seen, the leaching rate of PCP from the soil in the two systems was similar. In the initial weeks of the experiment, the leaching system was ineffective, but after day 28 when the pumping regimen was improved, the PCP was leached out of the soil. The data in FIGS. 5 and 6 are for shallow samples collected 1-3 inches from the soil surface. The soil was cleansed of 85% of its original PCP. Samples which were taken near the bottom of the soil (8-10 inches deep) between days 40 and 60 had higher PCP concentrations. From the limited amount of data obtained on these deep samples, the estimated deep PCP concentration is about twice as high as near the surface. Like the surface samples, these deep samples decreased in PCP concentration by about 100 ppm per week. The PCP which was leached from the soil in the bacterium-containing system did not accumulate in the leachate, indi-cating that it was metabolized as fast as it was extracted.

The invention has been described by reference to certain preferred embodiments and techniques. However, it should be understood that many variations and modifications may be made while remaining within the spirit and scope of the invention.

What is claimed is:

1. A method of detoxifying pentachlorophenol (PCP) by microbial degradation comprising culturing a PCP-degrading bacterium in an aqueous medium comprising dissolved PCP, wherein said bacterium is a member of the genus Flavobacterium, and is capable of sustained growth in medium concentrations of PCP between 250 mg/l and 400 mg/l as its sole source of carbon and energy.

2. The method of claim 1 wherein said method comprises inducing a PCP-degradation pathway of said bacterium by first culturing it in a first medium that is free of PCP and comprises a carbon and energy source other than PCP, and then adding an amount of PCP to said first medium.

3. The method of claim 2 wherein said source of carbon and energy is glutamic acid.

4. The method of claim 1 wherein said bacterium exhibits an insoluble yellow pigment.

5. The method of claim 1 wherein said bacterium is cultured at a temperature between 15° C. and 37° C.

6. The method of claim 1 wherein said bacterium has the characteristics of ATCC deposit No. 39723 and the mutations thereof.

7. A biologically pure culture of a strain of the genus Flavobacterium, wherein said strain exhibits sustained growth in media comprising pentachlorophenol (PCP) as the sole carbon and energy source at media PCP concentrations of 250-400 mg/l.

8. The culture of claim 7 wherein said strain exhibits an insoluble yellow pigment.

9. The culture of claim 7 wherein said strain is grown in said PCP-containing media at a temperature of about 20°-37° C.

10. The culture of claim 7, having the identifying characteristics of ATCC NO. 39723 and the mutations thereof.

* * * * *

UNITED STATES PATENT AND TRADEMARK OFFICE
CERTIFICATE OF CORRECTION

PATENT NO. : 4,713,340
DATED : December 15, 1987
INVENTOR(S) : Ronald L. Crawford It is certified that error appears in the above-identified patent and that said Letters Patent is hereby corrected as shown below:

At Col. 7, Table III, for "C (PCP, no bacteria) 0 100 90 47.5 12.5 7.5 0 0 0 0 0" read --C (PCP, no bacteria) 100 90 47.5 12.5 7.5 0 0 0 0 0--.

At Col. 7, Table III, for "D (PCP, plus bacteria) 77.5 77.5 100 100 100 100 100 95 90 85 80" read --D (PCP, plus bacteria) 100 100 100 100 100 95 90 85 80 77.5 77.5--.

At Col. 8, line 23, for "of leachage 27" read --of leachate 27--.

Signed and Sealed this

Twenty-eighth Day of June, 1988

Attest:

DONALD J. QUIGG

Attesting Officer

Commissioner of Patents and Trademarks